United States Patent
Meglan et al.

(10) Patent No.: US 11,058,288 B2
(45) Date of Patent: Jul. 13, 2021

(54) SYSTEMS AND METHODS FOR AMPLIFYING CHANGES IN A REGION OF INTEREST IN A SURGICAL ENVIRONMENT

(71) Applicant: Covidien LP, Mansfield, MA (US)

(72) Inventors: Dwight Meglan, Westwood, MA (US); Meir Rosenberg, Newton, MA (US)

(73) Assignee: COVIDIEN LP, Mansfield, MA (US)

( * ) Notice: Subject to any disclaimer, the term of this patent is extended or adjusted under 35 U.S.C. 154(b) by 581 days.

(21) Appl. No.: 15/767,006

(22) PCT Filed: Oct. 20, 2016

(86) PCT No.: PCT/US2016/057794
§ 371 (c)(1),
(2) Date: Apr. 9, 2018

(87) PCT Pub. No.: WO2017/070274
PCT Pub. Date: Apr. 27, 2017

(65) Prior Publication Data
US 2018/0296075 A1    Oct. 18, 2018

Related U.S. Application Data

(60) Provisional application No. 62/244,764, filed on Oct. 22, 2015.

(51) Int. Cl.
*A61B 1/00* (2006.01)
*A61B 1/313* (2006.01)
(Continued)

(52) U.S. Cl.
CPC ........ *A61B 1/00193* (2013.01); *A61B 1/0005* (2013.01); *A61B 1/00009* (2013.01);
(Continued)

(58) Field of Classification Search
CPC ........... G06T 7/0012; G06T 7/13; G06T 5/10; G06T 11/008; G06T 19/20; G06T 5/50;
(Continued)

(56) References Cited

U.S. PATENT DOCUMENTS 4,349,032 A * 9/1982 Koyata .............. A61B 1/00177
600/139
8,696,548 B2   4/2014 Gilboa
(Continued)

FOREIGN PATENT DOCUMENTS

JP           H0876027 A       3/1996

OTHER PUBLICATIONS

Chinese First Office Action dated Sep. 3, 2019 corresponding to counterpart Patent Application CN 201680059529.8.
(Continued)

*Primary Examiner* — James M Pontius

(57) ABSTRACT

The present disclosure is directed to systems and methods for amplifying a region of interest in a surgical environment. The system includes a stereo endoscope having a first camera and a second camera configured to obtain one or more images of the surgical environment. The system also includes a computer that has a central processing unit (CPU) configured to determine the region of interest in the surgical environment, a first controller configured to process the one or more images from the first camera to generate first amplified image(s), and a second controller configured to process the one or more images from the second camera to generate second amplified image(s). The first and second controllers process the one or more images based on the region of interest determined by the CPU. A display displays the one or more first amplified images and the one or more second amplified images.

22 Claims, 8 Drawing Sheets

(51) Int. Cl.
*A61B 1/045* (2006.01)
*A61B 1/05* (2006.01)
(52) U.S. Cl.
CPC ...... *A61B 1/00048* (2013.01); *A61B 1/00052* (2013.01); *A61B 1/045* (2013.01); *A61B 1/05* (2013.01); *A61B 1/313* (2013.01); *A61B 1/051* (2013.01)
(58) Field of Classification Search
CPC ......... G06T 19/006; G06T 2207/20024; G06T 2207/30004; G06T 2207/10048; G06T 2207/20221; A61B 90/36; A61B 90/37; A61B 2576/00; A61B 2090/365; H04N 5/232; H04N 5/33; H04N 5/23293
See application file for complete search history.

(56) References Cited

U.S. PATENT DOCUMENTS

| | | | |
|---|---|---|---|
| 9,610,133 | B2 | 4/2017 | Ma et al. |
| 10,152,789 | B2 | 12/2018 | Carnes et al. |
| 10,607,345 | B2 | 3/2020 | Carnes et al. |
| 2007/0140580 | A1 | 6/2007 | Heath et al. |
| 2008/0071143 | A1 | 3/2008 | Gattani et al. |
| 2010/0053213 | A1* | 3/2010 | Ishida ................... G06F 19/321 345/629 |
| 2012/0078236 | A1 | 3/2012 | Schoepp |
| 2012/0232343 | A1 | 9/2012 | Levy et al. |
| 2012/0289782 | A1 | 11/2012 | Viola |
| 2013/0329027 | A1 | 12/2013 | Igarashi |
| 2014/0072190 | A1 | 3/2014 | Wu et al. |
| 2014/0139616 | A1 | 5/2014 | Pinter et al. |
| 2015/0015480 | A1 | 1/2015 | Burr |
| 2016/0073853 | A1 | 3/2016 | Venkatesan et al. |
| 2017/0161893 | A1 | 6/2017 | Carnes et al. |

OTHER PUBLICATIONS

Chinese Second Office Action dated Jun. 2, 2020 corresponding to counterpart Patent Application CN 201680059529.8.
A. Jonathan McLeod et al.: "Motion Magnification for Endoscopic Surgery"; Process in Biomedical Optics and Imaging SPIE International Society for Optical Engineering; vol. 9036, 90360C1-8, publication date: Mar. 12, 2014.
International Search Report and Written Opinion of Int'l Appln. PCT/US2016/057794 dated Jan. 31, 2017.
Extended European Search Report dated Apr. 17, 2019 corresponding to counterpart Patent Application EP 16858176.7.

* cited by examiner

SYSTEMS AND METHODS FOR AMPLIFYING CHANGES IN A REGION OF INTEREST IN A SURGICAL ENVIRONMENT

CROSS-REFERENCE TO RELATED APPLICATIONS

This application is a U.S. National Stage Application filed under 35 U.S.C. § 371(a) of International Patent Application Serial No. PCT/US2016/057794, filed Oct. 20, 2016, which claims the benefit of and priority to U.S. Provisional Patent Application Ser. No. 62/244,764, filed Oct. 22, 2015, the entire disclosure of which is incorporated by reference herein.

BACKGROUND

Minimally invasive surgeries involve the use of multiple small incisions to perform a surgical procedure instead of one larger opening or incision. The small incisions have reduced patient discomfort and improved recovery times. The small incisions have also limited the visibility of internal organs, tissue, and other matter.

Endoscopes have been used and inserted in one or more of the incisions to make it easier for clinicians to see internal organs, tissue, and other matter inside the body during surgery. These endoscopes have included a camera with an optical and/or digital zoom capability that is coupled to a display showing the magnified view of organs, tissue, and matter inside the body as captured by the camera. However, in order to see high detail at a specific location inside the body, the endoscope has to be zoomed into the specific area whereby any peripheral vision of the endoscope is lost.

There is a need for providing a clinician with a detailed view of a specific location while presenting a broad view of the surgical environment.

SUMMARY

The present disclosure relates to surgical techniques to improve surgical outcomes for a patient, and more specifically, to systems and methods for enhancing a clinician's field of vision while performing a surgical technique.

In an aspect of the present disclosure, a system for amplifying specific changes in a region of interest in a surgical environment is provided. The system includes a stereo endoscope having a first camera and a second camera, each of the first camera and the second camera is configured to obtain one or more images of the surgical environment. The system also includes a computer having a central processing unit (CPU) configured to determine the region of interest or to work with a region of interest selected by a user in the surgical environment, a first controller configured to process the one or more images from the first camera to generate one or more first amplified images, wherein the first controller processes the one or more images based on the region of interest determined by the CPU or user, and a second controller configured to process the one or more images from the second camera to generate one or more second amplified images, wherein the first controller processes the one or more images based on the region of interest determined by the CPU or user. A display displays the one or more first amplified images and the one or more second amplified images.

In some embodiments, the CPU determines the region of interest based on a depth in the surgical environment. The depth is determined from the one or more images obtained from the first camera and the second camera which are then processed using techniques such as epipolar geometry. In some embodiments, the CPU determines the region of interest based on a location of a tool in the surgical environment.

In some embodiments, the first controller includes a spatial decomposition filter configured to decompose the one or more images from the first camera into a plurality of first spatial frequency bands, a temporal filter that is configured to be applied to the plurality of first spatial frequency bands to generate a plurality of first temporally filtered bands, an adder configured to add each band in the plurality of first spatial frequency bands to a corresponding band in the plurality of first temporally filtered bands to generate a plurality of first amplified bands, and a reconstruction filter configured to generate the one or more first amplified images by collapsing the plurality of first amplified bands.

In some embodiments, the second controller includes a spatial decomposition filter configured to decompose the one or more images from the second camera into a plurality of second spatial frequency bands, a temporal filter that is configured to be applied to the plurality of second spatial frequency bands to generate a plurality of second temporally filtered bands, an adder configured to add each band in the plurality of second spatial frequency bands to a corresponding band in the plurality of second temporally filtered bands to generate a second plurality of amplified bands, and a reconstruction filter configured to generate the one or more second amplified images by collapsing the plurality of second amplified bands.

In some embodiments, the first controller includes a color space decomposition filter configured to decompose the one or more images from the first camera into a plurality of first color space bands, a color filter that is configured to be applied to the plurality of first spatial frequency bands to generate a plurality of first color filtered bands, an adder configured to add each band in the plurality of first color space bands to a corresponding band in the plurality of first color filtered bands to generate a plurality of first color space amplified bands, and a reconstruction filter configured to generate the one or more first color space amplified images by collapsing the plurality of first color space amplified bands.

In some embodiments, the second controller includes a color space decomposition filter configured to decompose the one or more images from the second camera into a plurality of second color space bands, a color filter that is configured to be applied to the plurality of second color space bands to generate a plurality of second color filtered bands, an adder configured to add each band in the plurality of second spatial frequency bands to a corresponding band in the plurality of second color filtered bands to generate a second plurality of color space amplified bands, and a reconstruction filter configured to generate the one or more second color space amplified images by collapsing the plurality of second color space amplified bands.

The display includes a lens that displays the one or more first amplified images at a first location on the lens and displays the ore or more second amplified image at a second location on the lens different from the first location.

In another aspect of the present disclosure, a method for generating an amplified image of a region of interest in a surgical environment is provided. The method includes receiving one or more images of the surgical environment from a first camera, receiving one or more images of the surgical environment from a second camera, and determining the region of interest in the surgical environment. The method also includes generating one or more first amplified images from the one or more images from the first camera based on the determined region of interest and generating one or more second amplified images from the one or more images from the second camera based on the determined region of interest. The one or more first amplified images and the one or more second amplified images are then displayed.

In some embodiments, determining the region of interest is based on a depth in the surgical environment. The depth is determined from the one or more images received from the first camera and the second camera which are then processed using techniques such as epipolar geometry. In some embodiments, determining the region of interest is based on a location of a tool in the surgical environment.

In some embodiments, generating the one or more first amplified images includes decomposing the one or more images from the first camera into a plurality of first spatial frequency bands, applying a temporal filter to the plurality of first spatial frequency bands to generate a plurality of first temporally filtered bands, adding each band in the plurality of first spatial frequency bands to a corresponding band in the plurality of first temporally filtered bands to generate a plurality of first amplified bands, and collapsing the plurality of first amplified bands the one or more first amplified images.

In some embodiments, generating the one or more second amplified images includes decomposing the one or more images from the second camera into a plurality of second spatial frequency bands, applying a temporal filter to the plurality of second spatial frequency bands to generate a plurality of second temporally filtered bands, adding each band in the plurality of second spatial frequency bands to a corresponding band in the plurality of second temporally filtered bands to generate a plurality of second amplified bands, and collapsing the plurality of second amplified bands the one or more second amplified images.

In some embodiments, generating the one or more first amplified images includes decomposing the one or more images from the first camera into a plurality of first color space bands, applying a color filter to the plurality of first color space bands to generate a plurality of first color filtered bands, adding each band in the plurality of first color space frequency bands to a corresponding band in the plurality of first color filtered bands to generate a plurality of first amplified bands, and collapsing the plurality of first amplified bands the one or more first amplified images.

In some embodiments, generating the one or more second amplified images includes decomposing the one or more images from the second camera into a plurality of second color space bands, applying a color filter to the plurality of second spa color space bands to generate a plurality of second color filtered bands, adding each band in the plurality of second color space bands to a corresponding band in the plurality of second color filtered bands to generate a plurality of second color space amplified bands, and collapsing the plurality of second color space amplified bands to generate the one or more second color space amplified images.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Image data captured from a stereo endoscope during a surgical procedure may be analyzed to amplify color changes or movement within the stereo endoscope's field of view that may be difficult for a clinician to visualize in high detail. Various image processing technologies may be applied to this image data to identify different conditions in the patient. For example, Eulerian image amplification techniques may be used to identify wavelength or "color" changes of light in different parts of a capture image.

Phase-based motion amplification techniques may also be used to make motion or movement between image frames more visible to a clinician. In some instances, changes in a measured intensity of predetermined wavelengths of light between different image frames may be presented to a clinician to make the clinician more aware of the motion of particular objects of interest.

Eulerian image amplification and/or phase-based motion amplification technologies may be included as part of an imaging system. These technologies may enable the imaging system to provide higher detail for a specific location within a stereo endoscope's field of view and enhance surgical outcomes.

One or more of these technologies may be included as part of an imaging system in a surgical robotic system to provide a clinician with additional information within a stereo endoscope's field of view. This may enable the clinician to quickly identify, avoid, and/or correct undesirable situations and conditions during surgery.

The present disclosure is directed to systems and methods for providing amplified stereoscopic images in real time to a clinician during a surgical procedure. The systems and methods described herein apply image processing filters to an image stream to provide an amplified or enhanced image to a clinician via a display. In some embodiments, the systems and methods permit video capture during a surgical procedure. The captured video is processed in real time or near real time and then displayed to the clinician as an amplified stereoscopic image. The image processing filters are applied to each frame of the captured video. Providing the amplified image or video to the clinician provides the clinician with a detailed view of a specific location while presenting a broad view to a clinician.

The embodiments described herein enable a clinician to view a region of interest with sufficient detail to ensure the effectiveness of a surgical procedure.

Figure 1:
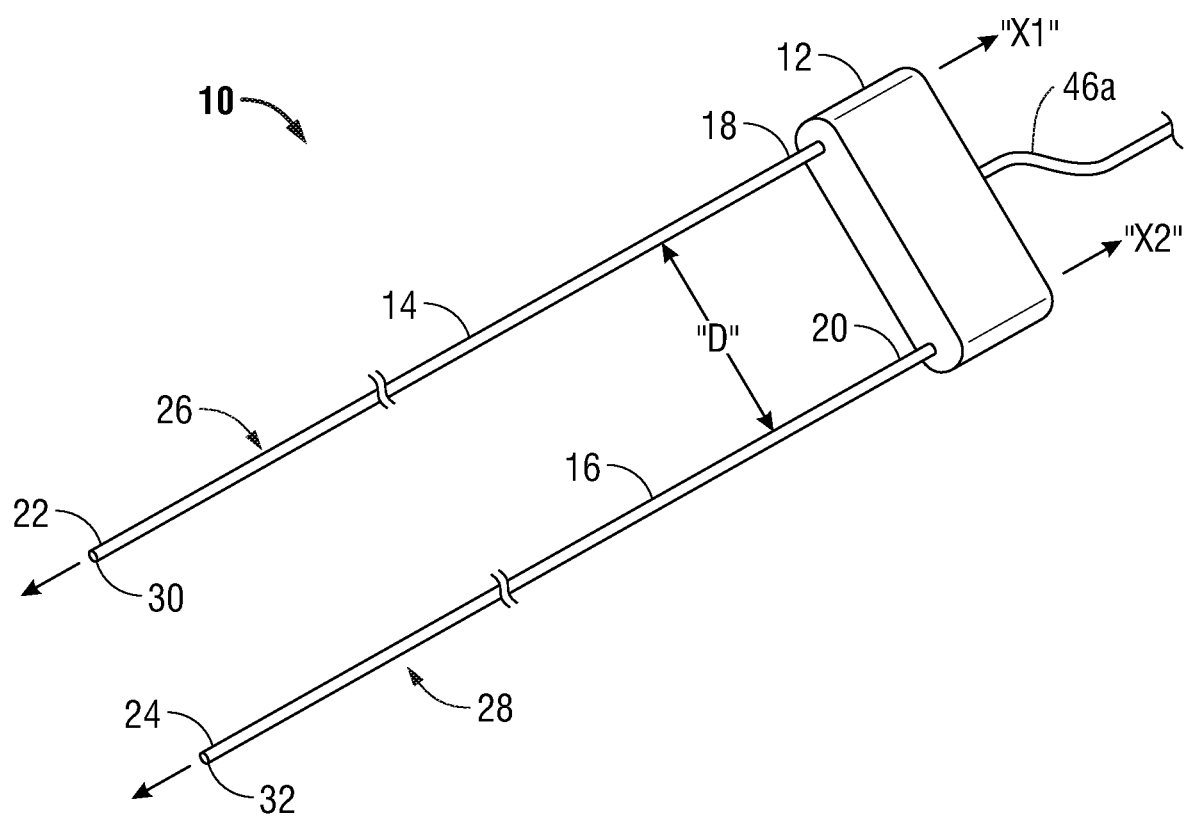
FIG. 1 is front, perspective view of a surgical camera assembly provided in accordance with the present disclosure.
Figure 2:
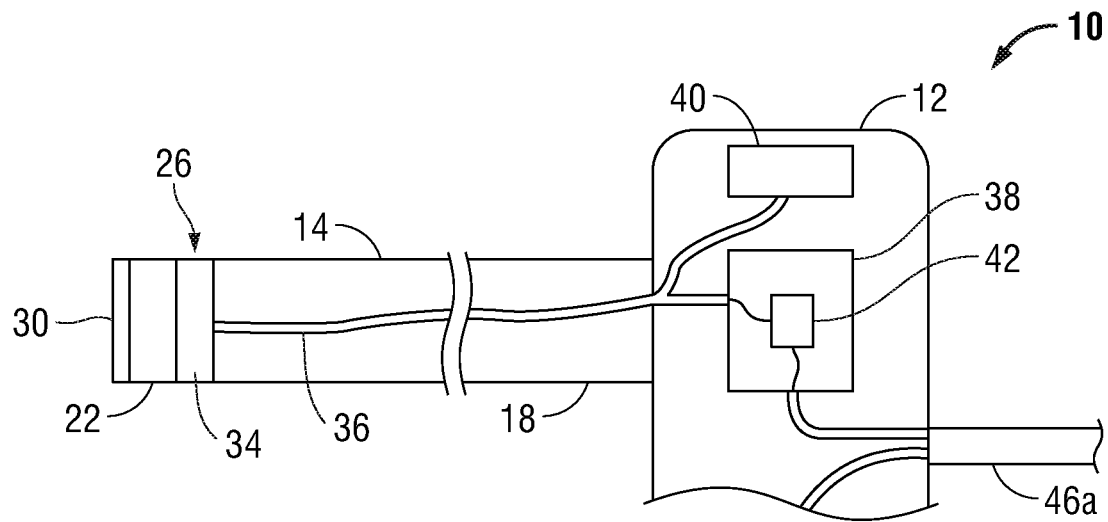
FIG. 2 is a longitudinal, cross-sectional view of a leg and a portion of a base of the surgical camera assembly of FIG. 1.
Figure 3:
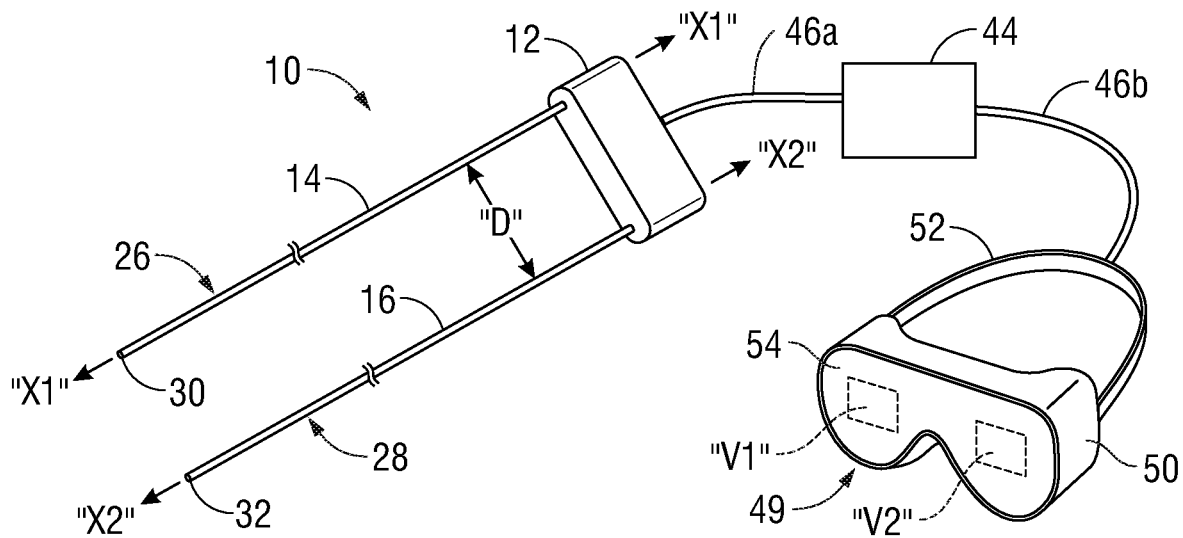
FIG. 3 is a perspective view of the surgical camera assembly of FIG. 1 shown coupled to a pair of visualization goggles.
Figure 9:
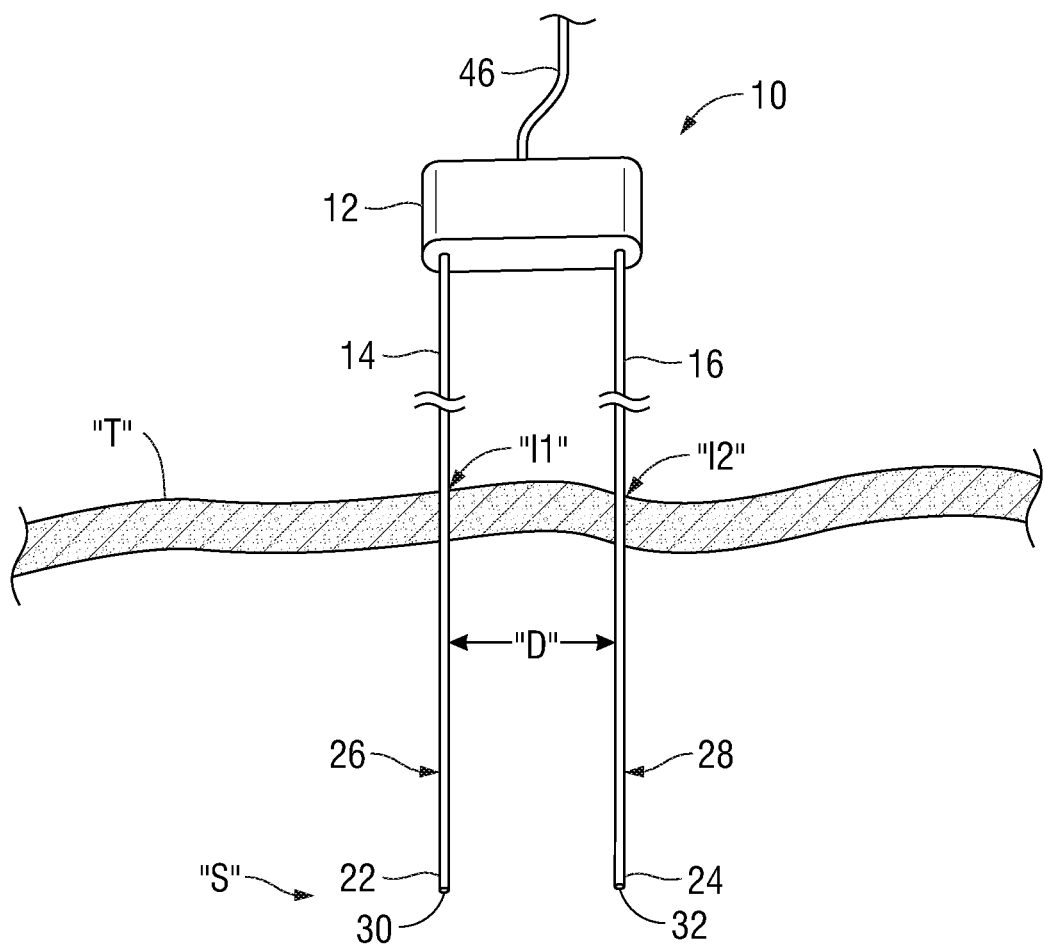
FIG. 9 is a partial cross-sectional view of the surgical camera assembly of FIG. 1 shown positioned within an internal surgical site.

Referring now to FIGS. 1-3, a stereo endoscope assembly provided in accordance with the present disclosure is shown and is generally identified by reference numeral 10. Exemplary stereo endoscopes that may be used with embodiments of the present disclosure include, but are not limited to, those described in U.S. patent application Ser. No. 13/442,009 entitled "TWIN CAMERA ENDOSCOPE" filed on Apr. 9, 2012, the contents of which are herein incorporated by reference. Stereo endoscope assembly 10 generally includes a base 12 having a pair of elongated legs 14, 16 extending distally therefrom. Legs 14, 16 are fixedly engaged to base 12 at proximal ends 18, 20, respectively, thereof and extend therefrom to free distal ends 22, 24, respectively, thereof. More particularly, legs 14, 16 are fixedly disposed in parallel, spaced-apart relation relative to one another to define a fixed distance "D," e.g., 5 mm, therebetween along the full lengths thereof. As will be described in greater detail below, each leg 14, 16 is configured for insertion through an incision "I1," "I2," respectively, formed within tissue "T" (see FIG. 9) and includes a respective surgical camera 26, 28 disposed therein. Surgical cameras 26, 28 cooperate to provide three-dimensional, or stereoscopic imaging of an internal surgical site "S" (FIG. 9).

With continued reference to FIG. 1, each leg 14, 16 defines a longitudinal axis "X1" and "X2," respectively, that, as a result of the parallel orientation of legs 14, 16, are parallel to one another. Each leg 14, 16 also includes a respective lens 30, 32 disposed at distal end 22, 24 thereof, that is configured to receive an image of the area extending distally from lenses 30, 32 along and radially outwardly from respective longitudinal axes "X1," "X2," of legs 14, 16, respectively. This configuration is employed such that the images received by lenses 30, 32 of surgical cameras 26, 28 of legs 14, 16, respectively, are of substantially the same area, but from different perspectives. In other words, the images received by surgical cameras 26, 28 are offset relative to one another by a distance "D," the distance between lenses 30, 32 of surgical cameras 26, 28 of legs 14, 16, respectively. Legs 14, 16 may each further include an illumination source (not shown) configured to illuminate the internal surgical site "S" (FIG. 9) to facilitate visualization thereof.

Cameras 26, 28 of legs 14, 16, respectively, are substantially similar to one another and, thus, only camera 26 will be described hereinbelow to avoid unnecessary repetition. Further, although one example of a camera 26 configured for use with stereo endoscope assembly 10 is described below, it is envisioned that any other suitable camera may be provided for use in conjunction with stereo endoscope assembly 10.

Continuing with reference to FIGS. 1-3, and to FIG. 2 in particular, camera 26 includes an image sensor 34 disposed within leg 14 that receives the optical image projected thereon by lens 30. Image sensor 34 is configured to convert the optical image received from lens 30 into an electrical signal. Image sensor 34 may be a CCD image sensor, a CMOS image sensor, or any other suitable image sensor as is known in the art.

With continued reference to FIG. 2, image sensor 34 is electrically coupled to an insulated wire, or bundle of wires 36, that extends from image sensor 34 proximally though leg 14 and into base 12 of stereo endoscope assembly 10. The image sensor (not shown) of camera 28 (FIG. 1) disposed within leg 16 (FIG. 1) similarly includes wire(s) (not shown) that extend proximally through leg 16 (FIG. 1) and into base 12. Wire(s) 36 transmit the electrical signal produced by image sensor 34 through leg 14 to control circuitry 38 disposed within base 12. Wire(s) 36 may also be configured to transfer power to image sensor 34 from a battery 40 disposed within base 12 or from an external power source (not explicitly shown). The wire(s) (not shown) of camera 28 (FIG. 1) are similarly configured for transmitting the electrical signal and/or power between the image sensor (not shown) of camera 28 (FIG. 1) and control circuitry (not shown) associated therewith that is disposed within base 12. Control circuitry 38 (and the control circuitry (not shown) associated with camera 28) may include a processor 42 that processes the electrical signal transmitted through wire(s) 36, e.g., converts the signal from analog to digital, and/or modulates the signal.

Control circuitry 38 and the control circuitry (not shown) associated with camera 28 then each transmit their respective signals, e.g., the converted and/or modulated signals, to a computer 44 via cable 46a. Alternatively, control circuitry 38 (and the control circuitry (not shown) associated with camera 300) may be configured to wirelessly transmit, or broadcast the processed signal to a wireless receiver (not explicitly shown) associated with the display 48.

Computer 44, as will be described in greater detail below, includes controllers 44A and 44B that receive images and/or video from cameras 26, 28, respectively, process the converted and/or modulated signals from the cameras 26, 28, respectively, and provide the processed signals to display 48 via cable 46b.

Display 48, as will be described in greater detail below, may be a pair of visualization goggles 49. However, it is envisioned that any other suitable display, e.g., a standard video monitor (not shown) may also be provided. For use with a standard video monitor (not shown), the signals from control circuitry 38 and the control circuitry (not shown) of camera 28 (FIG. 1) are multiplexed or synthesized, either within base 12, or externally, to produce an electronically synthesized three-dimensional video image for display on the video monitor (not shown).

As can be appreciated, in embodiments where battery 40 is disposed within base 12 for powering cameras 26, 28, and where base 12 is configured to wirelessly transmit the signal(s) to display 48, stereo endoscope assembly 10 need not require any external cables or wires, i.e. stereo endoscope assembly 10 may be fully wireless. One example of a wirelessly-configured surgical camera is disclosed in U.S. patent application Ser. No. 13/025,636, the entire contents of which are hereby incorporated by reference herein. Stereo endoscope assembly 10 may be similarly wirelessly-configured as described in U.S. patent application Ser. No. 13/025,636.

With reference now to FIG. 3, visualization goggles 49 are configured to be worn by the clinician and generally include a headset 50 and a support strap 52 configured to secure headset 50 on a clinician's head. Although FIG. 3 depicts a head mounted display, i.e., visualization goggles 49, display 48 may be any conventional stereo display. Headset 50 is positionable on the clinician's face and includes a lens 54, at least a portion of which is transparent so as not to substantially hinder the clinician's view when wearing visualization goggles 49. Headset 50 is configured to receive the electrical signals from computer 44 and to display each of the signals as video images.

The video images from cameras 26, 28, that are processed by computer 44, are displayed on lens 54 as video images "V1" and "V2," respectively. Control electronics (not explicitly shown) within headset 50 may be used to reposition the images "V1" and "V2" on lens 54 as desired for optimal viewing by the clinician and/or to make the images "V1" and "V2" transparent so as to permit the clinician to maintain visualization of the clinician's surroundings through lens 54 in addition to viewing the images "V1" and "V2." As described above, surgical cameras 26, 28 are independent of one another, with each surgical camera 26, 28 producing an image "V1" and "V2," respectively, for display to the clinician. However, in embodiments where a standard video monitor (not shown) is used in place of visualization goggles 49, control circuitry 38 of camera 26 and the control circuitry (not explicitly shown) of camera 28 may further be configured to multiplex, or synthesize the images produced by each of cameras 26, 28 to provide an electronically synthesized three-dimensional video image for display on the monitor (not shown) after being processed by computer 44.

Figure 4:
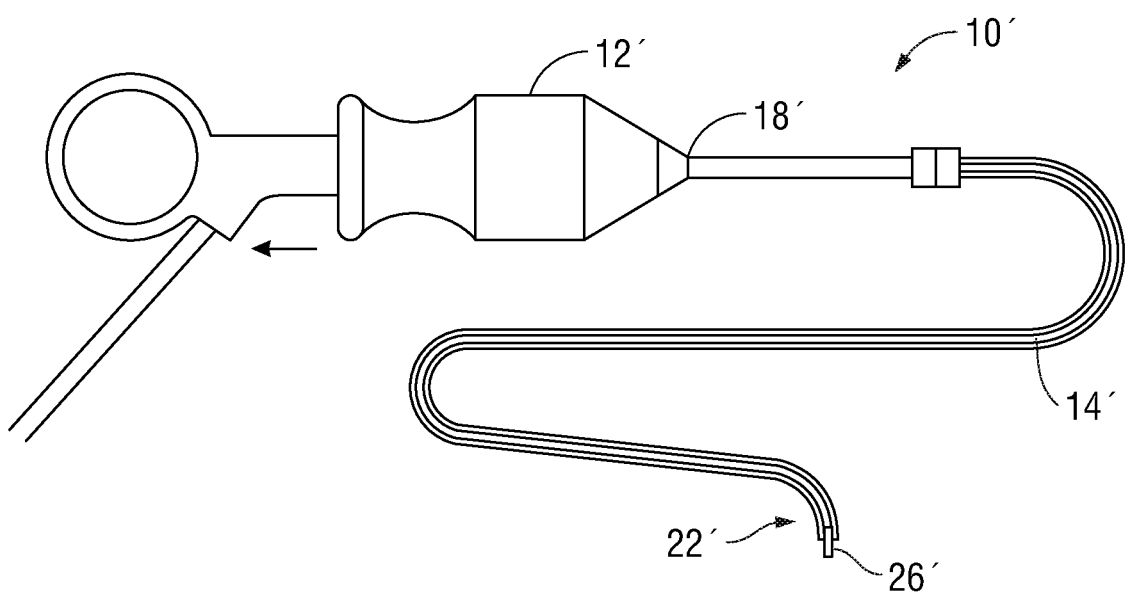
FIG. 4 is a side view of a surgical camera assembly in accordance with the present disclosure.

Referring now to FIG. 4, an endoscope assembly provided in accordance with the present disclosure is shown and is generally identified by reference numeral 10'. Exemplary endoscopes that may be used with embodiments of the present disclosure include, but are not limited to, those described in U.S. Pat. No. 8,696,548, the contents of which are herein incorporated by reference. Endoscope assembly 10' generally includes a base 12' having an elongated flexible shaft 14' extending distally therefrom. Shaft 14' is fixedly engaged to base 12 at proximal end 18', thereof and extend therefrom to free distal end 22'. Shaft 14' is configured for insertion through an incision, formed within tissue (not shown) and includes a surgical camera 26' that may be similar to surgical camera 26 described above. Surgical camera 26' provides imaging of an internal surgical site (not shown). In some embodiments, camera 26' may be an array camera capable of determining the depth of a specific location.

Figure 5:
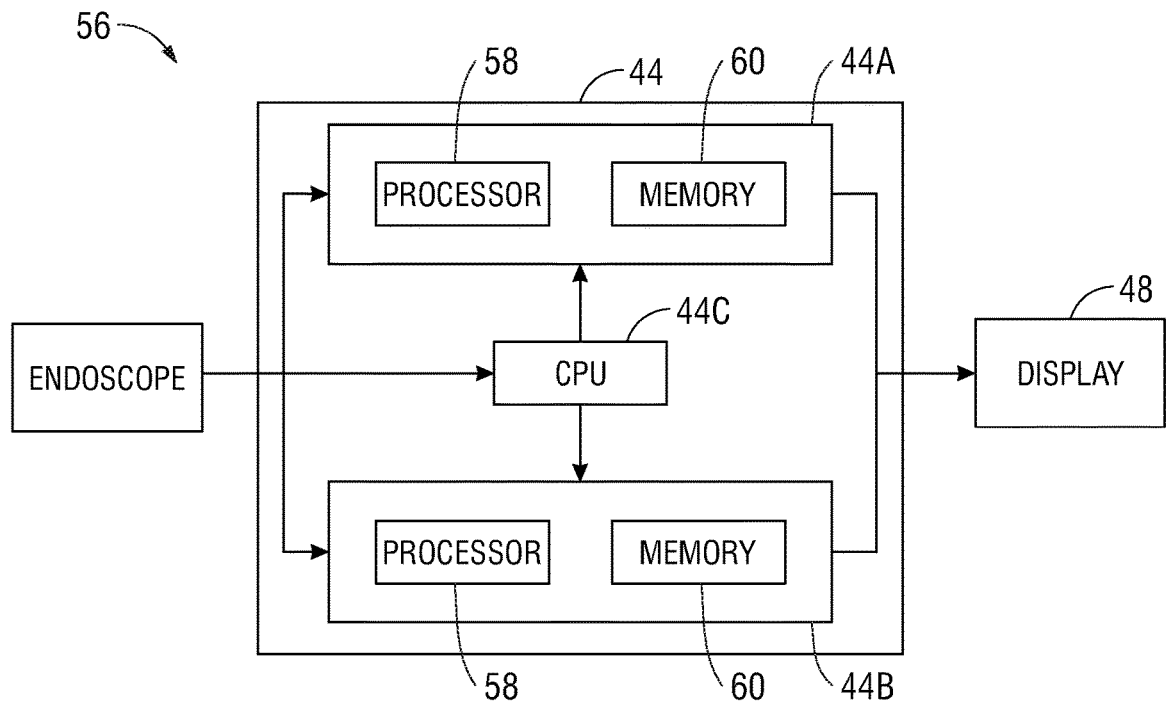
FIG. 5 is a block diagram of a system for augmenting a surgical environment in accordance with an embodiment of the present disclosure.

Turning to FIG. 5, a system for augmenting a surgical environment, according to embodiments of the present disclosure, is shown generally as 56. System 56 includes the computer 44, which includes controllers 44A and 44B and CPU 44C. Each controller 44A, 44B includes a processor 58 and a memory 60. The system 56 also includes an endoscope, which may be the stereo endoscope assembly 10 of FIG. 1 or the endoscope assembly 10' of FIG. 4. Display 48, displays amplified images to a clinician during a surgical procedure. In some embodiments, the computer 44 may communicate with a central server (not shown) via a wireless or a wired connection. The central server may store images of a patient or multiple patients that may be obtained using x-ray, a computed tomography scan, or magnetic resonance imaging. Controller 44A is configured to process video and/or images from camera 26 of stereo endoscope assembly 10 or camera 26' of endoscope assembly 10', while controller 44B is configured to process video and/or images from camera 28. CPU 44C determines a location in the region of interest to be amplified. The location may be determined by a position of one or more tool tips. In other embodiments, the location may be determined by a depth that is determined based on images from cameras 26, 28. The location and/or depth are provided to controllers 44A and 44B so that controllers 44A and 44B may perform image processing on the portion of the image corresponding to the location and/or depth. In other embodiments, the region of interest and/or depth may be selected by a user.

Figure 6:
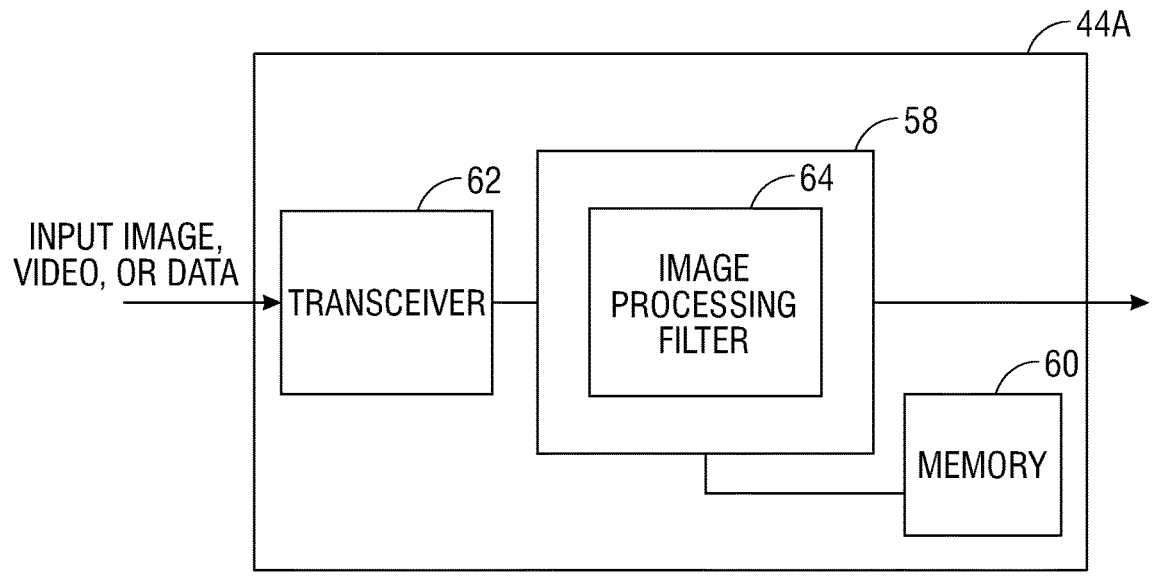
FIG. 6 is a system block diagram of the controller of FIG. 5.

Controllers 44A and 44B are substantially similar to one another and, thus, only controller 44A will be described hereinbelow with regard to FIGS. 6-8 to avoid unnecessary repetition. FIG. 5 depicts a system block diagram of the controller 44A. As shown in FIG. 6, the controller 44A includes a transceiver 62 configured to receive still frame images or video from the stereo endoscope assembly 10. In some embodiments, the transceiver 62 may include an antenna to receive the still frame images, video, or data via a wireless communication protocol. The still frame images, video, or data are provided to the processor 58. The processor 58 includes an image processing filter 64 that processes the received still frame images, video, or data to generate an amplified image or video. The image processing filter 64 may be implemented using discrete components, software, or a combination thereof. The amplified image or video is provided to the display 48.

Figure 7:
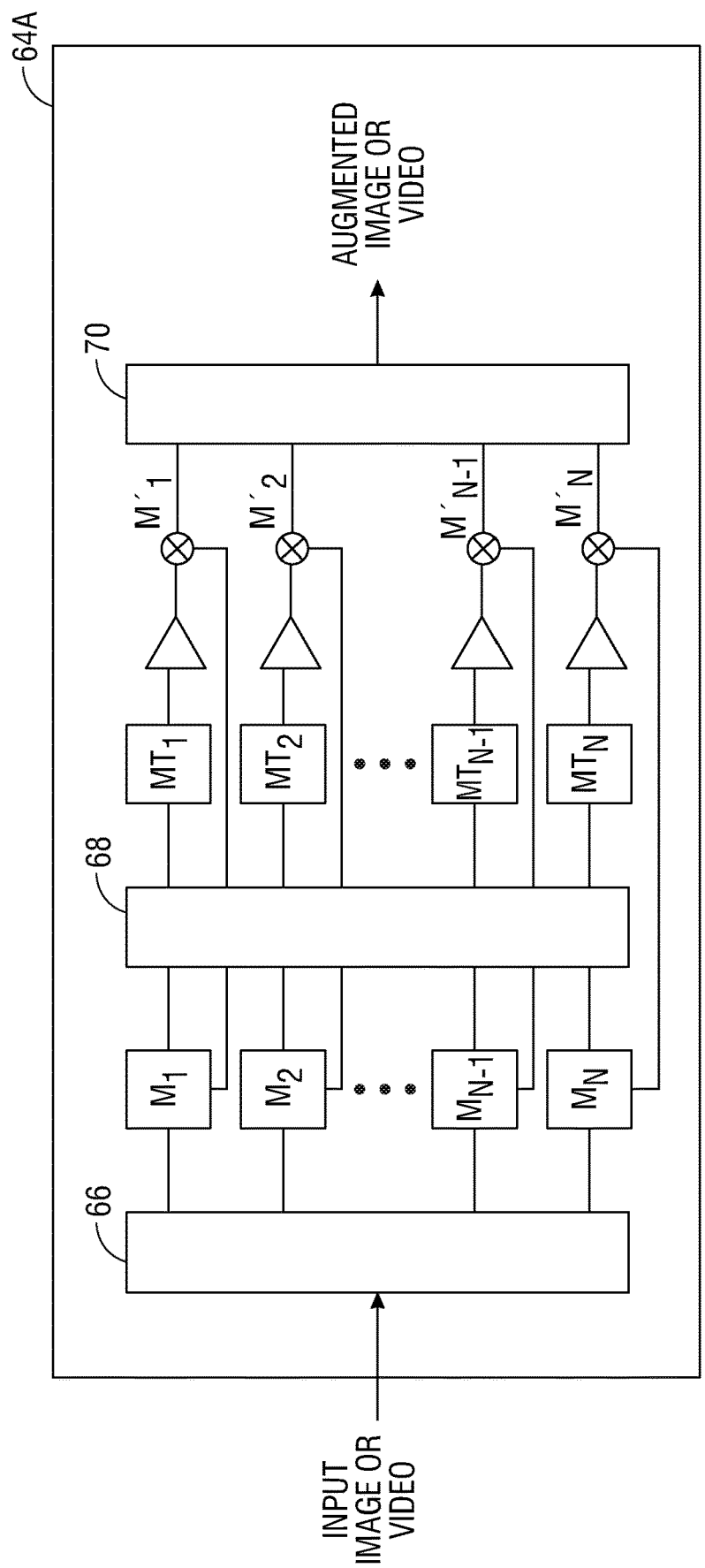
FIG. 7 is a block diagram of a system for augmenting an image or video in accordance with an embodiment of the present disclosure.

Turning to FIG. 7, a system block diagram of a motion amplification filter that may be applied to images and/or video received by transceiver 62 is shown as 64A. In the motion amplification filter 64A, each frame of a received video is decomposed into different spatial frequency bands $M_1$ to $M_N$ using a spatial decomposition filter 66. The spatial decomposition filter 66 uses an image processing technique known as a pyramid in which an image is subjected to repeated smoothing and subsampling.

After the frame is subjected to the spatial decomposition filter 66, a temporal filter 68 is applied to all the spatial frequency bands $M_1$ to $M_N$ to generate temporally filtered bands $MT_1$ to $MT_N$. The temporal filter 68 is a bandpass filter that is used to extract one or more desired frequency bands. For example, if the clinician is performing a suturing technique, the bandpass filter may be set to a frequency that corresponds to such movement. In other words, the bandpass filter is set to a narrow range that includes the suturing technique and applied to all the spatial frequency bands $M_1$ to $M_N$. Only the spatial frequency band that corresponds to the set range of the bandpass filter will be isolated or passed through.

All of the temporally filtered bands $MT_1$ to $MT_N$ are individually amplified by an amplifier having a distinct gain "a" per band. Because the temporal filter isolates or passes through a desired spatial frequency band, only the desired spatial frequency band gets amplified. The amplified temporally filtered bands $MT_1$ to $MT_N$ are then added to the original spatial frequency bands $M_1$ to $M_N$ to generate amplified bands $M'_1$ to $M'_N$.

Each frame of the video is then reconstructed using a reconstruction filter 70 by collapsing amplified bands $M'_1$ to $M'_N$ to generate an amplified frame. All the amplified frames are combined to produce the amplified video. The amplified video that is shown to the clinician includes a portion that is magnified, i.e., the portion that corresponds to the desired spatial frequency band, to enable the clinician to easily identify such portion.

In some embodiments, instead of using a motion amplifier to amplify the isolated color space filtered band, a color amplification filter 64B may highlight the color space filtered band using one or more colors before reconstructing the video. By setting the color amplification filter 64B to a specific color frequency band, the change in color of certain items, e.g., time cyclic blood perfused tissue, etc., may be highlighted in the display 48 permitting the clinician to easily perceive such items.

Figure 8:
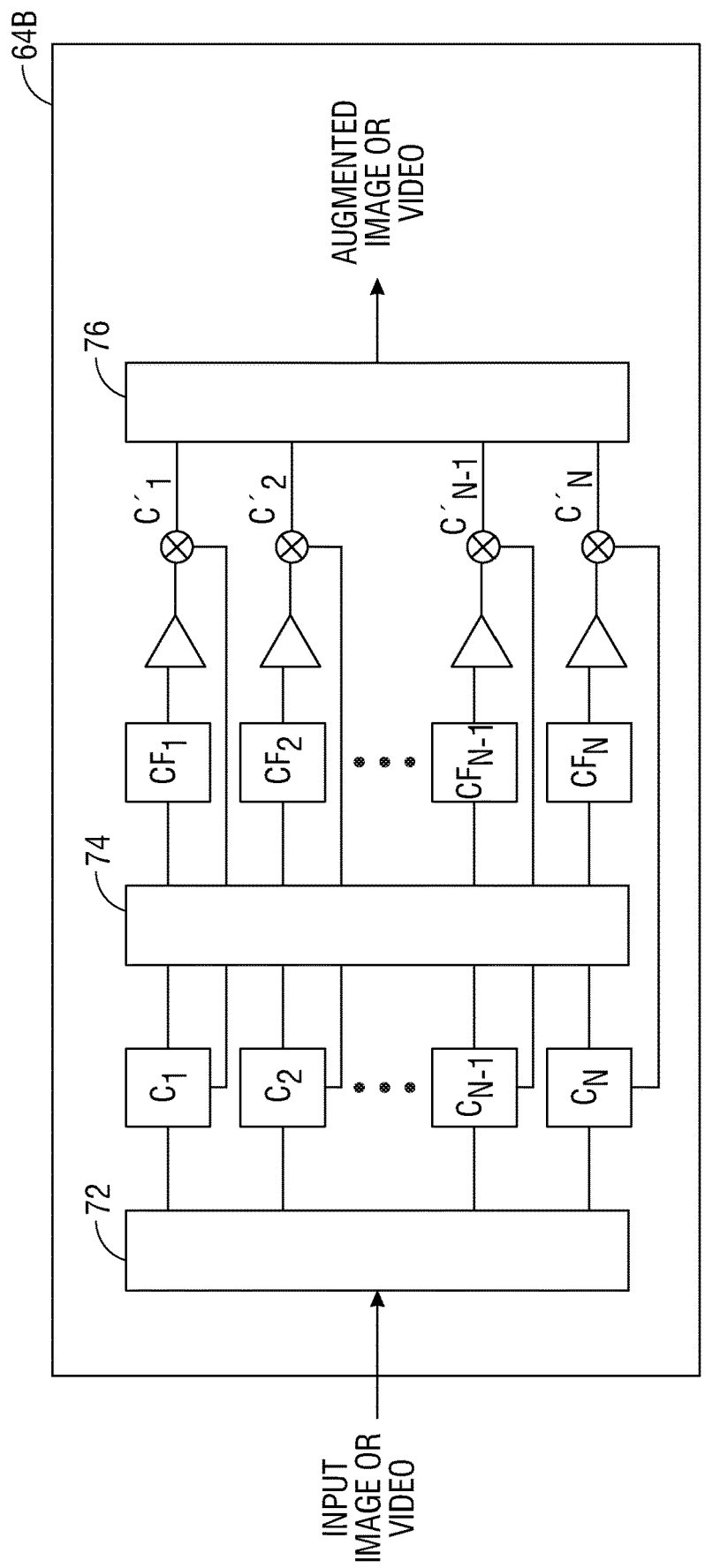
FIG. 8 is a block diagram of a system for augmenting an image or video in accordance with another embodiment of the present disclosure.

For example, FIG. 8 is a system block diagram of the color amplification filter 64B that may be applied to video received by transceiver 62. In the color amplification filter 64B, each frame of a received video is decomposed into different color space bands $C_1$ to $C_N$ using a color space decomposition filter 72. Similar to spatial decomposition filter 66, the decomposition filter 72 also uses an image processing technique known as a pyramid in which an image is subjected to repeated smoothing and subsampling.

After the frame is subjected to the color space decomposition filter 72, a color filter 74 is applied to all the color space bands $C_1$ to $C_N$ to generate color filtered bands $CF_1$ to $CF_N$. The color filter 68 is a bandpass filter that is used to extract one or more desired frequency bands. For example, if the clinician is performing a suturing technique that compresses tissue, the bandpass filter may be set to a frequency that corresponds to the color of blood such that the subtle change in the blood-centric color can be enhanced to make apparent the change in perfusion as a function of the suturing activity. In other words, the bandpass filter is set to a narrow range that includes that of blood perfused tissue and applied to all the color space bands $C_1$ to $C_N$. Only the color space band that corresponds to the set range of the bandpass filter will be isolated or passed through. Note that the converse can be done as well where the time cycle change in color at specific light frequency or a specific time frequency can be lessened such that the color change is considerably lessened in the observed image. This can allow other, non-time cyclic color changes to become more readily apparent to the observer.

All of the color filtered bands $C'_1$ to $C'_N$ are individually amplified by an amplifier having its own gain "α". Because the color filter isolates or passes through a desired color space band, only the desired color space band gets amplified. The amplified color space bands $CF_1$ to $CF_N$ are then added to the original color space bands $C_1$ to $C_N$ to generate amplified color space bands $C'_1$ to $C'_N$.

Each frame of the video is then reconstructed using a reconstruction filter 76 by collapsing the amplified color space bands $C'_1$ to $C'_N$ to generate an amplified frame. All the amplified frames are combined to produce the amplified video. The amplified video that is shown to the clinician includes a portion that is magnified, i.e., the portion that corresponds the desired color space band, to enable the clinician to easily identify such portion.

Turning now to FIG. 9, in conjunction with FIGS. 1-3 the use and operation of stereo endoscope assembly 10 is described. Initially, a pair of small punctures, or incisions "I1" and "I2" is formed through tissue "T." Incisions "I1" and "I2" are spaced-apart from one another the distance "D", e.g., 5 mm, between legs 14, 16 of stereo endoscope assembly 10 such that each leg 14, 16 may be inserted through one of the incisions "I1," "I2," respectively, and into the internal surgical site "S," while base 12 of stereo endoscope assembly 10 remains disposed externally of the internal surgical site "S." Once inserted into the surgical site "S," stereo endoscope assembly 10 may be manipulated, e.g., tilted, angled, or longitudinally translated, to better position lenses 30, 32 of surgical cameras 26, 28, respectively, within the internal surgical site "S."

Prior to, or once surgical cameras 26, 28 are positioned as desired, the clinician may activate display 48. Thereafter, surgical cameras 26, 28 can be activated to produce images "V1" and "V2," as viewed from distal ends 22, 24 of legs 14, 16, respectively, that are provided to computer 44. Computer 44 then amplifies the images "V1" and "V2" and displays the amplified images on display 48. As such, the clinician may perform a surgical task within the internal surgical site "S" (using other surgical instrumentation (not shown)) while visualizing the internal surgical site "S" in three dimensions. At the completion of the surgical task, or procedure, stereo endoscope assembly 10 may be withdrawn from incisions "I1" and "I2" formed within tissue "T." Due to the relatively small diameters of legs 14, 16 of stereo endoscope assembly 10 and, thus, the relatively small incisions "I1" and "I2" required to permit passage of legs 14, 16, respectively, therethrough, incisions "I1" and "I2" need not be sutured after removal of surgical camera assembly 10, but may simply be bandaged and allowed to heal naturally.

The above-described embodiments may also be configured to work with robotic surgical systems and what is commonly referred to as "Telesurgery." Such systems employ various robotic elements to assist the clinician in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

Figure 10:
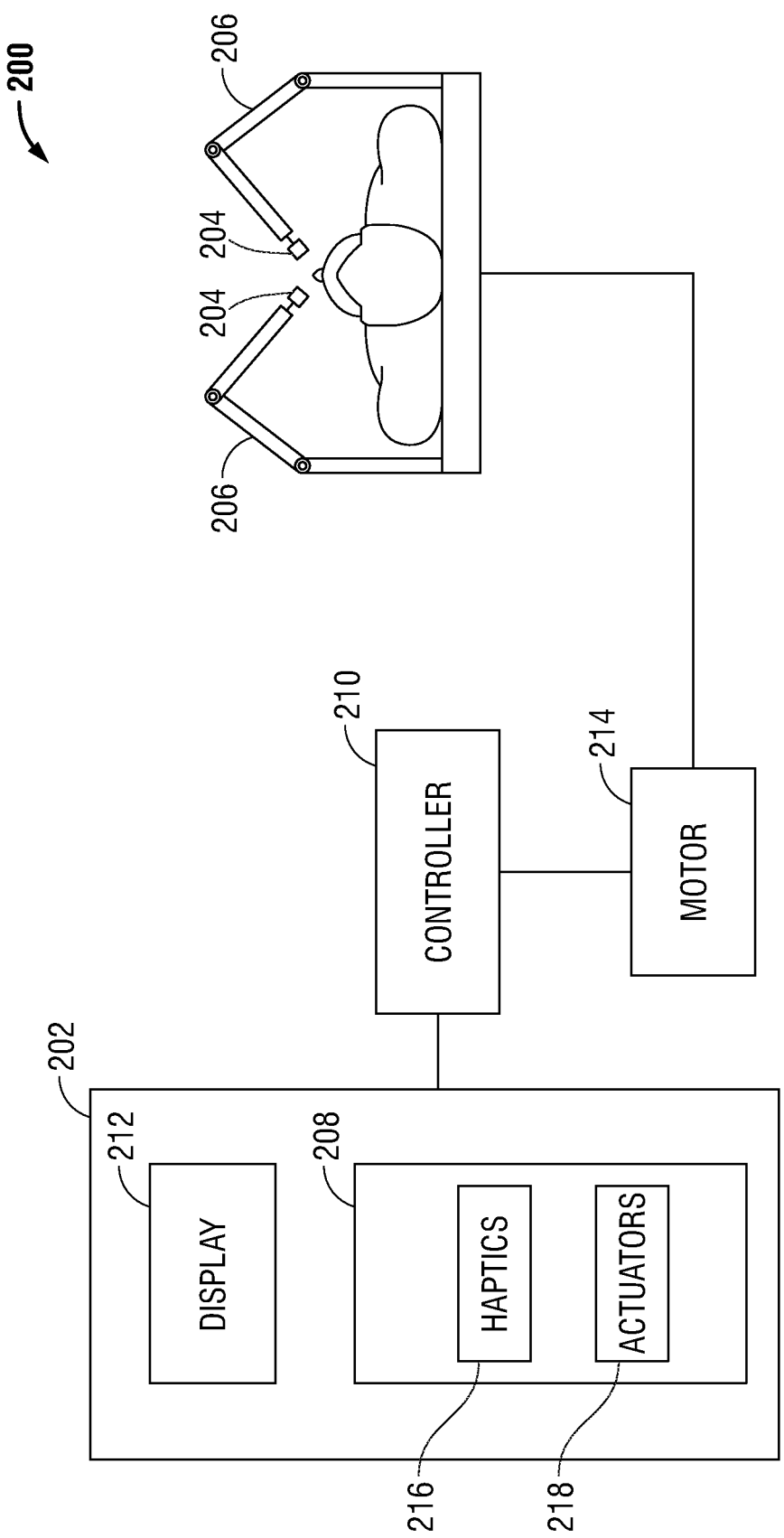
FIG. 10 is a system block diagram of a robotic surgical system in accordance with an embodiment of the present disclosure.

As shown in FIG. 10, a robotic surgical system 100 may be employed with one or more consoles 102 that are next to the operating theater or located in a remote location. In this instance, one team of clinicians or nurses may prep the patient for surgery and configure the robotic surgical system 100 with one or more instruments 104 while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

The robotic arms 106 of the surgical system 100 are typically coupled to a pair of master handles 108 by a controller 110. Controller 110 may be integrated with the console 102 or provided as a standalone device within the operating theater. The handles 106 can be moved by the clinician to produce a corresponding movement of the working ends of any type of surgical instrument 104 (e.g., probe, end effectors, graspers, knifes, scissors, etc.) attached to the robotic arms 106. For example, surgical instrument 104 may be a probe (not shown) that includes an image capture device. The probe is inserted into a patient in order to capture an image of a region of interest inside the patient during a surgical procedure. One or more of the image processing filters 64A or 64B are applied to the captured image by the controller 110 before the image is displayed to the clinician on a display 112.

The movement of the master handles 108 may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s) 204.

During operation of the surgical system 100, the master handles 108 are operated by a clinician to produce a corresponding movement of the robotic arms 106 and/or surgical instruments 104. The master handles 108 provide a signal to the controller 108 which then provides a corresponding signal to one or more drive motors 114. The one or more drive motors 114 are coupled to the robotic arms 106 in order to move the robotic arms 106 and/or surgical instruments 104.

The master handles 108 may include various haptics 116 to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such haptics 116 provide the clinician with enhanced tactile feedback simulating actual operating conditions. The haptics 116 may include vibratory motors, electroactive polymers, piezoelectric devices, electrostatic devices, subsonic audio wave surface actuation devices, reverse-electrovibration, or any other device capable of providing a tactile feedback to a user. The master handles 108 may also include a variety of different actuators 118 for delicate tissue manipulation or treatment further enhancing the clinician's ability to mimic actual operating conditions.

The embodiments disclosed herein are examples of the disclosure and may be embodied in various forms. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments," which may each refer to one or more of the same or different embodiments in accordance with the present disclosure. A phrase in the form "A or B" means "(A), (B), or (A and B)". A phrase in the form "at least one of A, B, or C" means "(A), (B), (C), (A and B), (A and C), (B and C), or (A, B and C)". A clinician may refer to a surgeon or any medical professional, such as a doctor, nurse, technician, medical assistant, or the like performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. For instance, any of the amplified images described herein can be combined into a single amplified image to be displayed to a clinician. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A system for amplifying a region of interest in a surgical environment, the system comprising:
    a stereo endoscope having a first camera and a second camera, each of the first camera and the second camera is configured to obtain an image stream of the surgical environment;
    a computer including:
        a central processing unit (CPU) configured to determine the region of interest in the surgical environment;
        a first controller configured to process the image stream from the first camera to generate a first amplified image stream, wherein the first controller processes the image stream based on the region of interest determined by the CPU; and
        a second controller configured to process the image stream from the second camera to generate a second amplified image stream, wherein the second controller processes the image stream based on the region of interest determined by the CPU; and
    a display configured to display the first amplified image stream and/or the second amplified image stream.

2. The system of claim 1, wherein the CPU determines the region of interest based on a depth in the surgical environment.

3. The system of claim 2, wherein the depth is determined from the image stream obtained from the first camera and/or the second camera.

4. The system of claim 1, wherein the CPU determines the region of interest based on a location of a tool in the surgical environment.

5. The system of claim 1, wherein the first controller includes:

a spatial decomposition filter configured to decompose the image stream from the first camera into a plurality of first spatial frequency bands;
a temporal filter that is configured to be applied to the plurality of first spatial frequency bands to generate a plurality of first temporally filtered bands;
an adder configured to add each band in the plurality of first spatial frequency bands to a corresponding band in the plurality of first temporally filtered bands to generate a plurality of first amplified bands; and
a reconstruction filter configured to generate the first amplified image stream by collapsing the plurality of first amplified bands.

6. The system of claim 5, wherein the second controller includes:
a spatial decomposition filter configured to decompose the image stream from the second camera into a plurality of second spatial frequency bands;
a temporal filter that is configured to be applied to the plurality of second spatial frequency bands to generate a plurality of second temporally filtered bands;
an adder configured to add each band in the plurality of second spatial frequency bands to a corresponding band in the plurality of second temporally filtered bands to generate a second plurality of amplified bands; and
a reconstruction filter configured to generate the second amplified image stream by collapsing the plurality of second amplified bands.

7. The system of claim 1, wherein the first controller includes:
a color space decomposition filter configured to decompose the image stream from the first camera into a plurality of first color space bands;
a color filter that is configured to be applied to the plurality of first color space bands to generate a plurality of first color filtered bands;
an adder configured to add each band in the plurality of first color space bands to a corresponding band in the plurality of first color filtered bands to generate a plurality of first color space amplified bands; and
a reconstruction filter configured to generate the one or more first amplified image stream by collapsing the plurality of first color space amplified bands.

8. The system of claim 7, wherein the second controller includes:
a color space decomposition filter configured to decompose the one or more images from the second camera into a plurality of second color space bands;
a color filter that is configured to be applied to the plurality of second color space bands to generate a plurality of second color filtered bands;
an adder configured to add each band in the plurality of second color space bands to a corresponding band in the plurality of second color filtered bands to generate a second plurality of color space amplified bands; and
a reconstruction filter configured to generate the second amplified image stream by collapsing the plurality of second color space amplified bands.

9. The system of claim 1, wherein the display displays the one or more first amplified images at a first location on the display and displays the one or more second amplified image at a second location on the display different from the first location.

10. A method for generating an amplified image of a region of interest in a surgical environment, the method comprising:
receiving a first image stream of the surgical environment from a first camera;
receiving a second image stream of the surgical environment from a second camera;
determining the region of interest in the surgical environment;
generating a first amplified image stream from the first image stream from the first camera based on the determined region of interest;
generating a second amplified image stream from the second image stream from the second camera based on the determined region of interest; and
displaying the first amplified image stream and/or the second amplified image stream.

11. The method of claim 10, wherein determining the region of interest is based on a depth in the surgical environment.

12. The method of claim 11, wherein the depth is determined from the first image stream and/or the second image stream received from the first camera or the second camera, respectively.

13. The method of claim 10, wherein determining the region of interest is based on a location of a tool in the surgical environment.

14. The method of claim 10, wherein generating the first amplified image stream includes:
decomposing the image stream from the first camera into a plurality of first spatial frequency bands;
applying a temporal filter to the plurality of first spatial frequency bands to generate a plurality of first temporally filtered bands;
adding each band in the plurality of first spatial frequency bands to a corresponding band in the plurality of first temporally filtered bands to generate a plurality of first amplified bands; and
collapsing the plurality of first amplified bands to generate the first amplified image stream.

15. The method of claim 14 wherein generating the second amplified image stream includes:
decomposing the image stream from the second camera into a plurality of second spatial frequency bands;
applying a temporal filter to the plurality of second spatial frequency bands to generate a plurality of second temporally filtered bands;
adding each band in the plurality of second spatial frequency bands to a corresponding band in the plurality of second temporally filtered bands to generate a plurality of second amplified bands; and
collapsing the plurality of second amplified bands to generate the second amplified image stream.

16. The method of claim 10, wherein generating the first amplified image stream includes:
decomposing the image stream from the first camera into a plurality of first color space bands;
applying a color filter to the plurality of first color space bands to generate a plurality of first color filtered bands;
adding each band in the plurality of first color space bands to a corresponding band in the plurality of first color filtered bands to generate a plurality of first color space amplified bands; and
collapsing the plurality of first color space amplified bands to generate the first amplified image stream.

17. The method of claim 16, wherein generating the second amplified image stream includes:
decomposing the image stream from the second camera into a plurality of second color space bands;

applying a color filter to the plurality of second color space bands to generate a plurality of second color filtered bands;

adding each band in the plurality of second color space bands to a corresponding band in the plurality of second color filtered bands to generate a plurality of second color space amplified bands; and collapsing the plurality of second color space amplified bands to generate the second amplified image stream.

18. A system for amplifying a region of interest in a surgical environment, the system comprising:

an endoscope having a camera configured to obtain an image stream of the surgical environment;

a computer including:
- a central processing unit (CPU) configured to determine the region of interest in the surgical environment, based on a depth in the surgical environment; and
- a controller configured to process the image stream from the camera to generate an amplified image stream, wherein the controller processes the image stream based on the region of interest determined by the CPU; and a display configured to display the amplified image stream.

19. The system of claim 18, wherein the depth is determined from the image stream obtained from the camera.

20. The system of claim 18, wherein the CPU determines the region of interest based on a location of a tool in the surgical environment.

21. A system for amplifying a region of interest in a surgical environment, the system comprising:

an endoscope having a camera configured to obtain an image stream of the surgical environment;

a computer including:
- a central processing unit (CPU) configured to determine the region of interest in the surgical environment; and
- a controller configured to process the image stream from the camera to generate an amplified image stream, wherein the controller processes the image stream based on the region of interest determined by the CPU, wherein the controller includes:
  - a spatial decomposition filter configured to decompose the image stream from the camera into a plurality of spatial frequency bands;
  - a temporal filter that is configured to be applied to the plurality of spatial frequency bands to generate a plurality of temporally filtered bands;
  - an adder configured to add each band in the plurality of spatial frequency bands to a corresponding band in the plurality of temporally filtered bands to generate a plurality of amplified bands; and
  - a reconstruction filter configured to generate the amplified image stream by collapsing the plurality of amplified bands; and a display configured to display the amplified image stream.

22. A system for amplifying a region of interest in a surgical environment, the system comprising:

an endoscope having a camera configured to obtain an image stream of the surgical environment;

a computer including:
- a central processing unit (CPU) configured to determine the region of interest in the surgical environment; and
- a controller configured to process the image stream from the camera to generate an amplified image stream, wherein the controller processes the image stream based on the region of interest determined by the CPU, wherein the controller includes:
  - a color space decomposition filter configured to decompose the image stream from the camera into a plurality of color space bands;
  - a color filter that is configured to be applied to the plurality of color space bands to generate a plurality of color filtered bands;
  - an adder configured to add each band in the plurality of color space bands to a corresponding band in the plurality of color filtered bands to generate a plurality of color space amplified bands; and
  - a reconstruction filter configured to generate the amplified image stream by collapsing the plurality of color space amplified bands; and a display configured to display the amplified image stream.

* * * * *